United States Patent
Fernot

(10) Patent No.: US 6,322,501 B1
(45) Date of Patent: Nov. 27, 2001

(54) TONSILLECTOMY RETRACTOR STABILIZER

(76) Inventor: Patricia C. Fernot, 1313 Greenpound Rd., Newfoundland, NJ (US) 07435

(*) Notice: Subject to any disclaimer, the term of this patent is extended or adjusted under 35 U.S.C. 154(b) by 0 days.

(21) Appl. No.: 09/572,656

(22) Filed: May 16, 2000

(51) Int. Cl.[7] .................................................. A61B 1/32
(52) U.S. Cl. ........................ 600/228; 600/234; 600/237
(58) Field of Search .................................. 600/201, 205, 600/227, 228, 229, 230, 235, 237, 234; 606/110; 5/600

(56) References Cited

U.S. PATENT DOCUMENTS

| | | | |
|---|---|---|---|
| 2,969,059 | * | 1/1961 | Meek et al. . |
| 4,143,652 | * | 3/1979 | Meier et al. ...................... 600/230 X |
| 4,380,999 | * | 4/1983 | Healy . |
| 5,092,314 | * | 3/1992 | Zeitels . |
| 5,520,608 | * | 5/1996 | Cabrera et al. ................... 600/227 X |
| 5,897,491 | * | 4/1999 | Kastenbauer et al. ........... 600/237 X |

* cited by examiner

*Primary Examiner*—Jeffrey A. Smith
(74) *Attorney, Agent, or Firm*—Alfred C. Hill

(57) ABSTRACT

A stabilizer for retractors employed in tonsillectomies includes a first longitudinal member secured to an operating table in an adjustable, substantially upright position; a second elongated member secured to the first elongated member adjacent an end thereof remote from the operating table at an adjustable angle relative to the first longitudinal member, the second longitudinal member having a plurality of notches spaced therealong to enable selection of one of the plurality of notches to receive an end of a retractor remote from a patient lying on the operating table; and an arrangement associated with both the first and second elongated members to enable adjustment of the adjustable angle to thereby enable the surgeon to manipulate the retractor and the head of the patient to place the head of the patient in a desired position to enable removal of the tonsils.

20 Claims, 2 Drawing Sheets

TONSILLECTOMY RETRACTOR STABILIZER

BACKGROUND OF THE INVENTION

The present invention relates to retractors employed in surgical procedures and more particularly to a stabilizer for retractors employed in tonsillectomies.

During tonsillectomies the tongue of the patient has to be retracted or held out of the way so that the surgeon can remove the tonsils. In the past, it has been the practice of using one of the surgical team to hold the retractor. This requires a lot of concentration on the part of the person holding the retractor and, as is known, it is very difficult for a person to hold anything without having the device being held moved, since the person cannot hold the same position for a great length of time.

Another type of retractor stabilization that could be used is a Mayo stand which is large and cumbersome.

SUMMARY OF THE INVENTION

An object of the present invention is to provide a simple, but effective retractor stabilizer employed in tonsillectomies.

Another object of the present invention is to provide a tonsillectomy retractor stabilizer eliminating the necessity of employing one of the surgical team to hold the retractor while the surgeon is performing the tonsillectomy.

A feature of the present invention is the provision of a stabilizer for retractors employed in tonsillectomies comprising a first elongated member; a first means to secure the first elongated member to an operating table in an adjustable, substantially upright position; a second elongated member secured to the first elongated member adjacent an end thereof remote from the operating table at an adjustable angle relative thereto, the second elongated member having a plurality of second means spaced therealong to enable selection of one of the plurality of second means to receive an end of a retractor remote from a patient lying on the operating table; and third means associated with both the first and second elongated members to enable adjustment of the adjustable angle to thereby enable a surgeon to manipulate the retractor and head of a patient to place the head of the patient in a desired position.

BRIEF DESCRIPTION OF THE DRAWING

Above-mentioned and other features and objects of the present invention will become more apparent by reference to the following description taken in conjunction with the accompanying drawing, in which.

DESCRIPTION OF THE PREFERRED EMBODIMENTS

Figure 1:
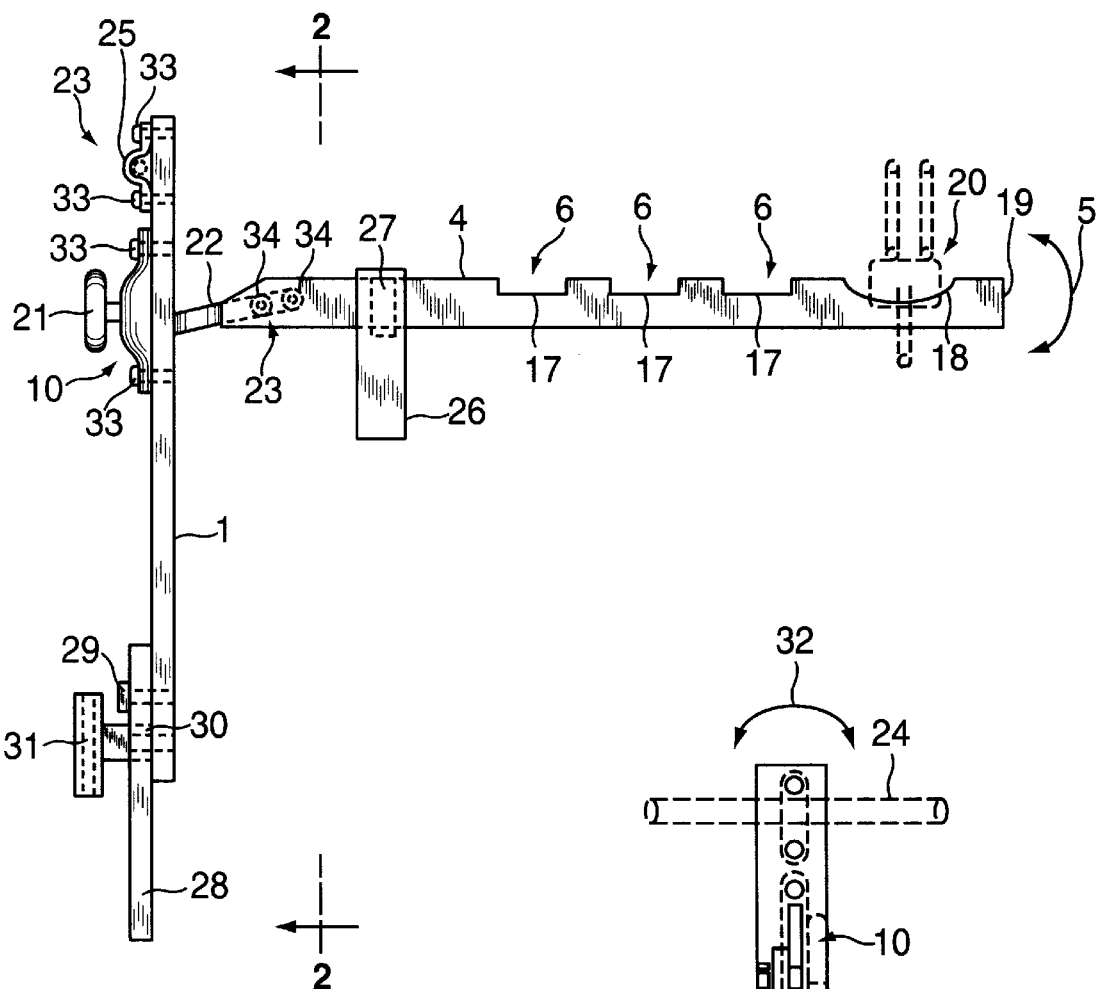
FIG. 1 is a plan view of the retractor stabilizer in accordance with the principles of the present invention.
Figure 2:
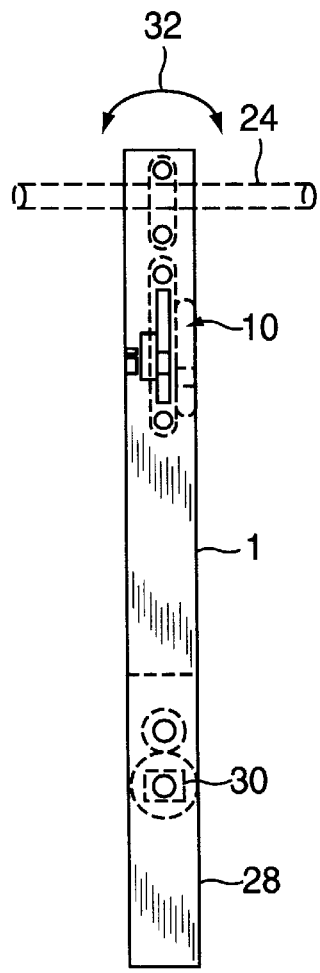
FIG. 2 is a view taken along line 2—2 of FIG. 1 in accordance with the principles of the present invention.

Referring to FIGS. 1–4, the stabilizer for a retractor employed in tonsillectomies in accordance with the principles of the present invention includes a first elongated member 1, a first means 2 to secure the first longitudinal member 1 to an operating table 3 in an adjustable, substantially upright position. A second elongated member 4 is secured to the first elongated member 1 adjacent an end thereof remote from the operating table 3 at an adjustable angle relative to member 1 as indicated by arrow 5. The elongated member 4 includes a plurality of second means 6 spaced therealong to enable selection of one of the plurality of second means 6 to receive an end 7 of a retractor 8 remote from a patient 9 lying on the operating table 3. A third means 10 is associated with both the members 1 and 4 to enable adjustment of the adjustable angle to thereby enable a surgeon to manipulate retractor 8 and head 11 of the patient 9 to place head 11 of the patient 9 in a desired position to enable accomplishing the removal of the tonsils.

Figure 3:
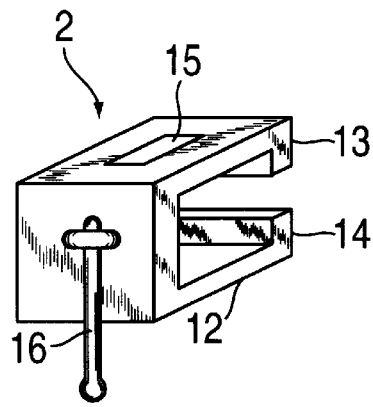
FIG. 3 is a perspective view of a clamp that is employed with the retractor stabilizer of FIGS. 1 and 2 to fasten the stabilizer to the operating table.
Figure 4:
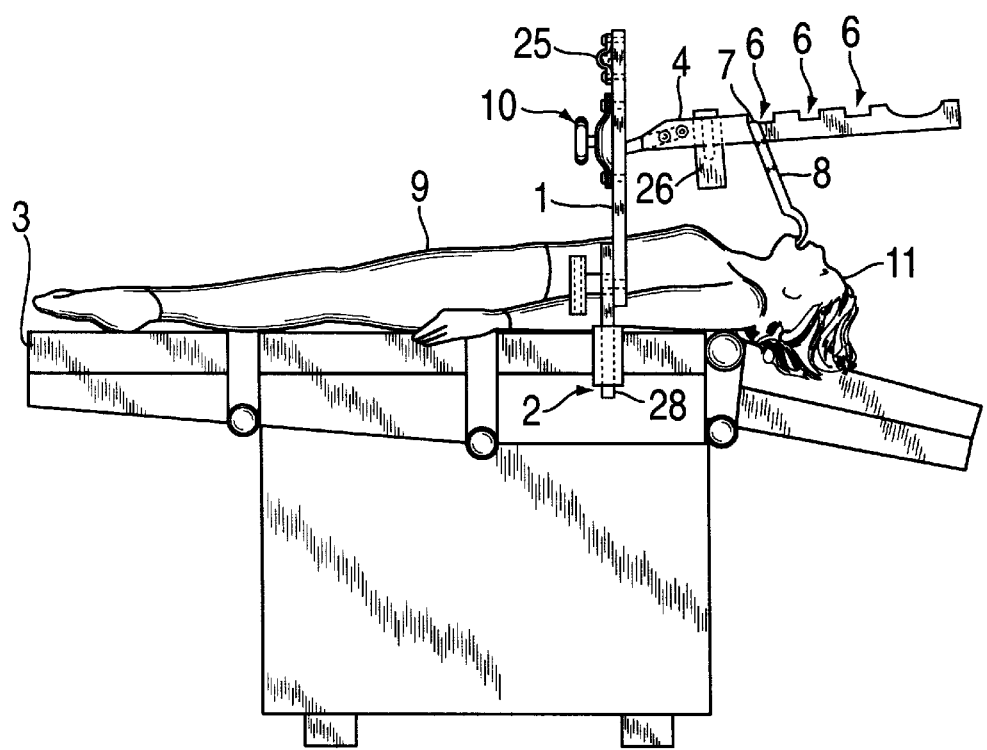
FIG. 4 is a plan view of the retractor stabilizer employed in relation with the patient in accordance with the principles of the present invention.

The first means 2, more clearly shown in FIG. 3, includes a U-shaped member 12 having opposed end portions 13 and 14 to engage an edge of operating table 3. A slot 15 is provided in both legs of U-shaped portion 12 to receive an end of elongated member 1 adjacent operating table 3. Slot 15 enables moving member 1 up or down to adjust the height of member 4. A clamping mechanism 16 is provided to secure the U-shaped member 12 and the elongated member 1 to the operating table 3.

As illustrated in the FIG. 1 in greater detail, the plurality of second means 6 includes a plurality of notches 17 to enable the end 7 of the retractor 8 to be selectively placed in one of the notches 17 at the surgeons discretion. Also an additional notch 18 is provided between notches 17 and the end 19 of member 4 to stabilize and support an anesthesia circuit.

The third means 10 includes a crank arrangement having a crank 21 and a lever 22 connected to member 4 at 23. The crank arrangement is secured to member 3 and connected to the member 4 by lever 22 to enable adjustment of the adjustable angle. The crank arrangement may be a window crank or the like.

The stabilizer in accordance with the principles of the present invention includes a means 23 disposed on the first member 1 above the third means 10 to organize surgical wires and tubes 24 used during a tonsillectomy. The fourth means 23 may be in the form of a clip arrangement, or as shown in FIG. 1 a loop 25, that will hold the surgical wires and tubes 24 during a tonsillectomy in an organized relationship so as not to interfere with the surgeon during the course of removing the tonsils from the patient.

A container 26 contains a clip 27 enabling container 26 to be clipped to member 4. Container 26, which would be sterilized, enables the surgeon to park surgical equipment therein for ease of access during the tonsillectomy. Such surgical equipment might include a suction wand and a cauterizing instrument.

Member 1 includes a portion 28 that is pivoted to member 1 at 29 and includes a slot 30 in which the shaft of knob 31 is capable of sliding. This arrangement enables member 1 and, hence, member 4 to be tilted toward patient 9 as indicated by arrow 32 in FIG. 2. Tightening of knob 31 holds member 1 in the tilted relationship desired by the surgeon.

As can be seen from the foregoing the surgeon and/or the surgical team has a plurality of adjustment that can be made to the retractor stabilizer so that the retractor can be positioned as desired by the surgeon for ease of extracting the patient tonsils.

Means 10 and loop 25 are fastened to member 1 by bolts 33 which are threaded into a tapped holes in member 1, or by bolts passed through untapped holes in member 1 and secured in place by lock nuts.

Member 4 is fastened to lever 22 by bolts 34 secured by lock nuts.

In a prototype, the members 1 and 4 are made of stainless steel and with member 1 being 1"×7/16"×23" and the member 4 being 1"×7/16"×17". The 23" length of member 1 includes 19" of main body on the top of the member 1, on the opposite side relative to the working arm 4 is a loop 25. Directly below this, on the same side of the member 1 is crank arrangement which controls the working arm or member 4. Approximately half way along the working arm or member 4 are three notched areas 17 measuring 1"×¼" and the additional notch 18 measuring 2"×½".

While I have described above the principles of my invention in connection with specific apparatus, it is to be clearly understood that this description is made only by way of example and not as a limitation to the scope of my invention as set forth in the objects thereof and in the accompanying claims.

I claim:

1. A stabilizer for retractors employed in tonsillectomies comprising:
    a first elongated member secured to an operating table in an adjustable, substantially, upright position;
    a second elongated member secured to said first elongated member adjacent an end thereof remote from said operating table at an adjustable angle relative thereto, said second elongated member having a plurality of first means spaced therealong to enable selection of one of said plurality of first means to receive an end of a retractor remote from a patient lying on said operating table; and
    second means associated with both said first and second elongated members to enable adjustment of said adjustable angle to thereby enable a surgeon to manipulate said retractor and head of said patient to place said head of said patient in a desired position.

2. A stabilizer according to claim 1, wherein
said plurality of first means include
    a plurality of notches spaced along said second elongated member to enable said end of said retractor remote from said patient to be selectively placed in one of said plurality of notches at the discretion of said surgeon.

3. A stabilizer according to claim 2, wherein
said second means includes
    a crank means disposed on said first elongated member and connected to said second elongated member to enable adjustment of said adjustable angle.

4. A stabilizer according to claim 3, wherein
said second elongated member further includes
    a third means disposed between said plurality of first means and an end of said second elongated member remote from said first elongated member to stabilize and support an anesthesia circuit.

5. A stabilizer according to claim 4, wherein
said third means includes
    an additional notch large enough to stabilize and support said anesthesia circuit.

6. A stabilizer according to claim 1, wherein
said second means includes
    a crank means disposed on said first elongated member and connected to said second elongated member to enable adjustment of said adjustable angle.

7. A stabilizer according to claim 6, wherein
said second elongated member further includes
    a third means disposed between said plurality of first means and an end of said second elongated member remote from said first elongated member to stabilize and support an anesthesia circuit.

8. A stabilizer according to claim 7, wherein
said third means includes
    an additional notch large enough to stabilize and support said anesthesia circuit.

9. A stabilizer according to claim 1, wherein
said second elongated member further includes
    a third means disposed between said plurality of first means and an end of said second elongated member remote from said first elongated member to stabilize and support an anesthesia circuit.

10. A stabilizer according to claim 9, wherein
said third means includes
    a notch large enough to stabilize and support said anesthesia circuit.

11. A stabilizer according to claim 1, further including
    a third means disposed on said first elongated member above said second means to organize surgical wires and tubes used during a tonsillectomy.

12. A stabilizer according to claim 1, further including a container removably clipped to said second elongated member adjacent said first elongated member to hold equipment employed during a tonsillectomy.

13. A stabilizer according to claim 1, wherein said first elongated member further includes an arrangement adjacent said operating table to enable tilting said first elongated member and, hence, said second elongated member toward said patient.

14. A stabilizer according to claim 13, wherein said plurality of first means include a plurality of notches spaced along said second elongated member to enable said end of said retractor remote from said patient to be selectively placed in one of said plurality of notches at the discretion of said surgeon.

15. A stabilizer according to claim 14, wherein said second means includes a crank means disposed on said first elongated member and connected to said second elongated member to enable adjustment of said adjustable angle.

16. A stabilizer according to claim 15, wherein
said second elongated member further includes
    a third means disposed between said plurality of notches and an end of said second elongated member remote from said first elongated member to stabilize and support an anesthesia circuit.

17. A stabilizer according to claim 16, wherein
said third means includes
    an additional notch large enough to stabilize and support said anesthesia circuit.

18. A stabilizer according to claim 17, further including
    a fourth means disposed on said first elongated member above said second means to organize surgical wires and tubes during a tonsillectomy.

19. A stabilizer according to claim 18, further including
    a container removably clipped to said second elongated member adjacent said first elongated member to hold equipment employed during a tonsillectomy.

20. A stabilizer according to claim 13, further including
    a container removably clipped to said second elongated member to hold equipment employed during a tonsillectomy.

* * * * *